(12) United States Patent
Bojarski et al.

(10) Patent No.: US 9,726,541 B2
(45) Date of Patent: Aug. 8, 2017

(54) ELECTROMAGNETIC RADIATION SENSOR FOR MONITORING A MEDIUM

(71) Applicant: AB Elektronik Sachsen GmbH, Klingenberg (DE)

(72) Inventors: Aldo Bojarski, Höckendorf (DE); Klaus Erler, Lübeck (DE); Katrin Künzelmann, Dresden (DE); Andre Legner, Dresden (DE); Paul Smith, Cambridge (GB); Tobby Straßberger, Höckendorf (DE)

(73) Assignee: AB Elektronik Sachsen GmbH, Klingenberg (DE)

( * ) Notice: Subject to any disclaimer, the term of this patent is extended or adjusted under 35 U.S.C. 154(b) by 0 days.

(21) Appl. No.: 14/975,792

(22) Filed: Dec. 20, 2015

(65) Prior Publication Data
US 2016/0178437 A1  Jun. 23, 2016

Related U.S. Application Data

(63) Continuation of application No. 13/824,417, filed as application No. PCT/EP2011/066128 on Sep. 16, 2011, now abandoned.

(30) Foreign Application Priority Data

Sep. 21, 2010 (DE) .......................... 10 2010 041 141
Sep. 21, 2010 (DE) .......................... 20 2010 012 771

(51) Int. Cl.
*G01J 3/28* (2006.01)
*G01J 3/02* (2006.01)
(Continued)

(52) U.S. Cl.
CPC ........... *G01J 3/2803* (2013.01); *G01J 3/0291* (2013.01); *G01J 3/10* (2013.01); *G01J 3/14* (2013.01);
(Continued)

(58) Field of Classification Search
CPC .... G01J 3/0291; G01J 3/10; G01J 3/14; G01J 3/2803; G01N 21/27; G01N 21/41;
(Continued)

(56) References Cited

U.S. PATENT DOCUMENTS 5,015,091 A * 5/1991 Suzuki .................. G01N 21/43
356/135
9,188,528 B2 * 11/2015 Bojarski ............ G01N 21/4133
(Continued)

FOREIGN PATENT DOCUMENTS

DE          4033087 A1 * 4/1992  ......... G01N 21/4133

*Primary Examiner* — Kara E Geisel
*Assistant Examiner* — Violeta A Prieto
(74) *Attorney, Agent, or Firm* — Gudrun E. Huckett

(57) ABSTRACT

A sensor for monitoring a medium has an electromagnetic radiation source, mirrors, and a detector for electromagnetic radiation arranged inside a cup-shaped housing part. The cup-shaped part has flat, angularly arranged wall areas defining a cavity in which, outside of the housing, the medium is contained. The flat wall areas are transparent for electromagnetic radiation and arranged in the beam path from the electromagnetic radiation source to the detector so that the electromagnetic radiation passes through first wall, medium in the cavity, and second wall. The first and second wall areas and the medium form a refracting prism. A cover closes off the cup-shaped part so that electromagnetic radiation source, detector, and mirrors are enclosed in the housing. A data processing system is connected to electromagnetic radiation source and detector so that electromagnetic radiation of different wavelengths is refracted in the prism and the resulting spectra are detected and evaluated.

4 Claims, 1 Drawing Sheet

(51) Int. Cl.
*G01J 3/14* (2006.01)
*G01J 3/10* (2006.01)
*G01N 21/41* (2006.01)
*G01N 21/27* (2006.01)

(52) U.S. Cl.
CPC ......... *G01N 21/27* (2013.01); *G01N 21/4133* (2013.01); *G01N 2201/0221* (2013.01); *G01N 2201/0627* (2013.01)

(58) Field of Classification Search
CPC ....... G01N 21/4133; G01N 2201/0221; G01N 2201/0627; G01N 21/8507
See application file for complete search history.

(56) References Cited

U.S. PATENT DOCUMENTS

| | | | | |
|---|---|---|---|---|
| 2008/0239317 A1* | 10/2008 | Schulkin | .................. | G01J 4/00 356/365 |
| 2009/0103076 A1* | 4/2009 | Gloeckner | ......... | G01N 21/4133 356/137 |
| 2013/0271756 A1* | 10/2013 | Bojarski | ............ | G01N 21/4133 356/300 |
| 2015/0036125 A1* | 2/2015 | Bojarski | ............ | G01N 21/4133 356/128 |

* cited by examiner

ELECTROMAGNETIC RADIATION SENSOR FOR MONITORING A MEDIUM

CROSS-REFERENCE TO RELATED APPLICATIONS

This application is a continuation application of U.S. patent application Ser. No. 13/824,417 having a date of completion of all 35 USC 371 requirements of 4 Jun. 2013, said application Ser. No. 13/824,417 being a national stage filing of international application No. PCT/EP2011/066128 having an international filing date of 16 Sep. 2011 and designating the United States, said international application claiming a priority date of 21 Sep. 2010, based on the two prior filed German patent applications No. 20 2010 012 771.8 and No. 10 2010 041 141.8, the entire contents of the aforesaid United States patent application, the international application, and the aforesaid two German patent applications being incorporated herein by reference.

BACKGROUND OF THE INVENTION

The invention concerns sensors for monitoring a medium, comprising at least one electromagnetic radiation source and a detector for electromagnetic radiation wherein the medium is located in the beam path between the electromagnetic radiation source and the detector.

The publication DE 10 2007 010 805 B3 discloses a method and a device for determining the urea concentration of a solution. For this purpose, light is emitted at various incident angles onto a boundary surface between a denser medium and a less dense medium, i.e., the body and the solution. For this purpose, a boundary surface between the body and the solution must be present. The light is then partially reflected at the boundary surface, depending on the incident angle, wherein with increasing incident angle the proportion of light reflected at the boundary surface increases. The reflected radiation is then detected by an appropriately arranged spatially resolving radiation detector.

The publication DE 10 2008 056 559 A1 comprises a sensor arrangement for detection of a first liquid medium in a second liquid medium by means of reflection of an emitted light beam as well as a correlated receiver. For this purpose, two glass rod lenses encapsulated in a housing are arranged parallel to each other. The glass rod lenses have a different optical refractive index than the liquid media. Opposite the glass rod lenses a reflection surface is arranged that is connected to the housing.

It is disadvantageous that depositions and contaminations of the boundary surface or of the reflection surface can falsify the measured result.

SUMMARY OF THE INVENTION

The invention has the object to monitor the material composition of a medium in a simple way.

This object is solved in that the electromagnetic radiation source and the detector are arranged in at least one housing, in that the housing has two flat wall areas that are angularly arranged relative to each other and are transparent for the electromagnetic radiation so that these wall areas and the medium located at the wall areas form a prism that refracts the electromagnetic radiation, and in that the detector has at least a one-dimensional sensor with photo diodes for the refracted electromagnetic radiation, wherein a spectrum that changes with a change of the medium is detectable.

The sensors for monitoring a medium comprising at least one electromagnetic radiation source and a detector for electromagnetic radiation, wherein the medium is in the beam path between the electromagnetic radiation source and the detector, are characterized by their simple realization.

For this purpose, the electromagnetic radiation source and the detector are arranged in at least one housing. Moreover, the housing has two flat wall areas that are positioned angularly relative to each and are transparent for the electromagnetic radiation so that these wall areas and the medium that is located at the wall areas form a prism that refracts the electromagnetic radiation. Moreover, the detector is at least one one-dimensional sensor with photo diodes for the refracted electromagnetic radiation, wherein a spectrum that changes as the medium changes is detectable.

By means of the sensor, medium is monitored by means of the transmitted light principle. By means of the prism, the electromagnetic radiation is refracted at the incident surface and the exit surface as a function of the wavelength. The result is a spectrum of the electromagnetic radiation source. Upon a change of the medium the refraction of the electromagnetic radiation, in particular upon passing through the wall areas, changes so that a changed spectrum is produced also. The position of spectral lines will shift so that the location of the electromagnetic radiation of a specific wavelength impinging on the detector changes. This is detected by the detector so that a change of the medium is detected. This is realized, for example, by means of a known data processing system which is connected to the detector. In this context, the data processing system is in particular a known microcomputer.

A further advantage resides in that contaminations on the housing which would otherwise lead to an intensity change have no effect on the detection. The same applies to components in the medium that make the medium turbid. Decisive for the detection is the incident location of the electromagnetic radiation and not its intensity. Accordingly, even aging processes of the radiation source and of the detector have no effect on the sensor for monitoring a medium.

Moreover, the sensor is characterized in that only the medium is outside of the housing. All components of the sensor are arranged within the housing so that a compact sensor exists. In the simplest case, for this purpose the electromagnetic radiation source and the detector are positioned opposite each other, wherein a space for the medium is positioned therebetween.

Advantageous embodiments of the invention are disclosed in the dependent claims.

In the beam path downstream of the electromagnetic radiation source, at least one device is arranged that guides and/or deflects the radiation so that the electromagnetic radiation source and the detector can be positioned adjacent to each other. The configuration is simplified substantially. The electromagnetic radiation source and the detector are positioned on a carrier adjacent to each other.

Favorably, mirrors or total-reflecting prisms constitute the radiation-deflecting device so that the radiation is deflected twice in sequence. The electromagnetic radiation source is advantageously arranged for this purpose relative to the medium above the detector. The medium is positioned in this context between the device and the detector. In this way, a very simple and compact configuration for the sensor is provided.

The device that is guiding the radiation is a light-wave conductor. When the light-wave conductor has in this context preferably a U-shape, the radiation of the electromagnetic radiation source impinges on the adjacently positioned detector.

According to one embodiment, electromagnetic radiation sources for radiations of different wavelength and the detector are connected to a data processing system so that sequentially radiation of different wavelength can be refracted in the prism and the resulting spectra can be detected and evaluated. For this purpose, the electromagnetic radiation sources are preferably operated in a cycled fashion so that a spatial shift of individual spectral lines can be detected. The sensitivity of the sensor is increased.

The data processing system is a data processing system that determines respectively the location of the electromagnetic radiation of a specific wavelength impinging on the detector. Changes of the medium can be detected easily by the determination of location.

In the beam path downstream of the electromagnetic radiation source a device is arranged that influences the electromagnetic radiation so that electromagnetic radiation of a specific wavelength penetrates the medium and reaches the detector. This is in particular a filter or a screen. The sensitivity of the sensor is increased.

According to one embodiment, a first part of the housing is a cup-shaped formed part comprised of a material that is transparent for the radiation. The first part has moreover a recess for the medium. The housing is closed off by a cover as the second part of the housing. In the first part, at least the electromagnetic radiation source and the detector are arranged. The area of the housing with the recess or the cutout is placed in the medium so that the medium is also located in the recess or the cutout. By means of the wall areas of the recess or of the cutout that are angularly arranged relative to each other, the radiation is coupled out and, after passing the medium, is coupled in.

Beneficially, the formed part is monolithic. Accordingly, it is possible to provide sensors that can be economically beneficially realized.

Beneficially, the medium is an aqueous solution so that the concentration of at least one substance is detectable in the aqueous solution.

BRIEF DESCRIPTION OF THE DRAWINGS

One embodiment of the invention is illustrated in the drawings in principle, respectively, and will be explained in more detail in the following.

It is shown in.

DESCRIPTION OF PREFERRED EMBODIMENTS

A sensor for monitoring a medium is comprised substantially of an electromagnetic radiation source 1, a detector 2, a device 3 deflecting the radiation, and a housing 5.

Figure 1:
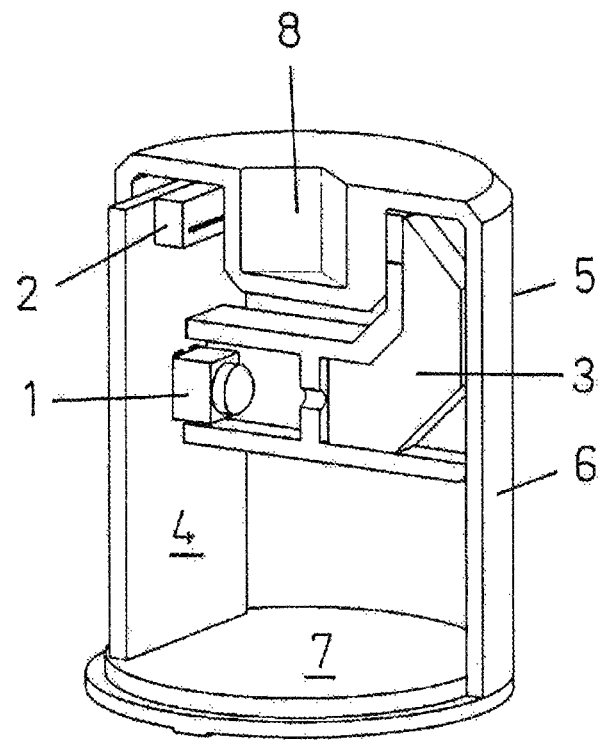
FIG. 1 a sensor for monitoring a medium in a longitudinal section.

FIG. 1 shows a sensor for monitoring a medium in a longitudinal section in a principal illustration.

The medium is, for example, an aqueous solution. As is known, as the electromagnetic radiation source 1 a luminescence diode 1 and as the detector 2 a CCD sensor 2 with photo diodes are used, wherein CCD stands for charge-coupled device. The latter is embodied as a one-dimensional (line) or two-dimensional (matrix) CCD sensor 2.

The luminescence diode 1 and the CCD sensor 2 are arranged adjacent to each other on a circuit board 4 as a carrier.

The circuit board 4 is located in a first part 6 of the housing 5. This first part 6 is cup-shaped and is comprised of a material that is transparent for the radiation of the luminescence diode 1. Moreover, this first part 6 is a monolithically embodied formed part which has a cutout 8/a recess for the medium.

In the beam path downstream of the luminescence diode 1, a radiation-deflecting device 3 with two total-reflecting prisms is arranged so that the radiation is deflected in sequence twice by 90 degrees. The entry of the device 3 is arranged in the plane of the luminescence diode 1 so that its electromagnetic radiation is coupled into the device 3. The exit for coupling out the electromagnetic radiation of the luminescence diode 1 that has been twice deflected by 90 degrees is arranged in the plane of the CCD sensor 2. Between the device 3 and CCD sensor 2 there is the cutout 8 for the medium so that through the wall areas of the cutout 8 the electromagnetic radiation penetrates the space, formed by the cutout 8, with the medium. The wall areas are designed flat and are arranged angularly relative to each other. The angle enclosing the wall areas is smaller than 180 degrees. The wall areas are moreover arranged relative to the electromagnetic radiation such that in connection with the medium a prism that refracts the electromagnetic radiation is provided.

The optical elements are arranged such that the spectrum of the radiation impinges on the CCD sensor 2. In this context, the location of pre-determined spectral lines is detected. When the composition of the medium changes, the refraction will change also. The spectral lines of the radiation are shifted. By means of the CCD sensor 2, this shift can be determined spatially.

This can be done also with regard to the change of electromagnetic radiation of a specific wavelength. In this connection, an electromagnetic radiation source 1 with at least one specific wavelength is used.

By using a multi-color luminescence diode 1 as an electromagnetic radiation source 1, electromagnetic radiation of a specific wavelength can be realized in a simple way.

In a first embodiment, the luminescence diode 1 is arranged at a spacing relative to the medium above the CCD sensor 2 (illustration of FIG. 1).

In the second embodiment, the luminescence diode 1 is arranged at a spacing adjacent CCD sensor 2.

Figure 2:
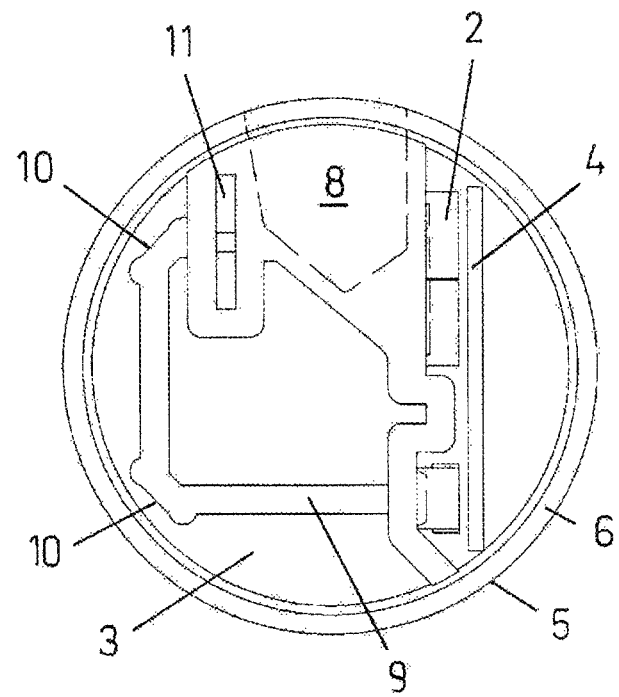
FIG. 2 a sensor in a section illustration.

FIG. 2 shows in this connection a sensor in a principal section illustration.

In the beam path downstream of the luminescence diode 1, the radiation-deflecting device 3 with devices 10 for deflecting the radiation in the form of mirrors 10 is arranged in a light-guiding passage 9 so that the radiation in sequence is deflected twice by 90 degrees. The radiation-deflecting device 3 and the first part 6 of the housing 5 can be configured to be of a multi-part or single-part configuration. The luminescence diode 1, the CCD sensor 2, the device 3, and the cutout 8 are located in one plane. In a variant of this second embodiment, a slit diaphragm 11 is a component of the device 3.

For controlling the measurement and evaluation of the measured results, the electromagnetic radiation source 1 and the CCD sensor 2 are connected to a data processing system. It is a known microcomputer on the circuit board 4 with a microcontroller as a central processing unit.

The second part 7 of the housing 5 is a cover so that an overall enclosed sensor for monitoring the medium is realized.

What is claimed is:

1. A sensor for monitoring a medium comprising:
   at least one electromagnetic radiation source configured to emit electromagnetic radiation;
   a detector for electromagnetic radiation;
   a housing comprised of a first part and a second part, wherein the first part is a cup-shaped monolithic formed part comprised of a material transparent for the electromagnetic radiation;
   wherein the electromagnetic radiation source and the detector are arranged adjacent to each other in an interior of the cup-shaped monolithic formed part of the housing;
   the cup-shaped monolithic formed part of the housing comprising a first flat wall area and a second flat wall area that are angularly arranged relative to each other and project into the interior of the cup-shaped monolithic formed part to define a cavity in which, outside of the housing, the medium is immediately contained, wherein the first and second flat wall areas are transparent for the electromagnetic radiation and are arranged in a beam path of the electromagnetic radiation from the electromagnetic radiation source to the detector such that the electromagnetic radiation passes sequentially through the first wall, through the medium in the cavity outside of the housing, and through the second wall, wherein the first and second wall areas and the medium form a prism refracting the electromagnetic radiation;
   a radiation-deflecting device arranged in the interior of the cup-shaped monolithic formed part of the housing in the beam path downstream of the electromagnetic radiation source, the radiation deflecting device comprising a first mirror and a second mirror arranged at a right angle relative to each other such that the electromagnetic radiation is deflected twice in sequence first by 90° at the first mirror and then again by 90° at the second mirror in the beam path from the electromagnetic radiation source to the detector;
   wherein the prism is arranged in the beam path downstream of the second mirror and upstream of the detector;
   the detector comprising photo diodes, arranged in a row or in a matrix, for the refracted electromagnetic radiation;
   wherein the second part is a cover closing off the first part so that the sensor is an enclosed sensor in which the electromagnetic radiation source, the detector, and the first and second mirrors are enclosed in the housing;
   a data processing system, wherein the electromagnetic radiation source and the detector are connected to the data processing system so that sequentially electromagnetic radiation of different wavelengths are refracted in the prism and the resulting electromagnetic radiation spectra are detected and evaluated, wherein a change of the electromagnetic radiation spectra changing with a change of the medium is detectable;
   wherein the data processing system determines the change of the medium based on shifts in the location of the different wavelengths of the electromagnetic radiation reaching the detector, respectively.

2. The sensor according to claim 1, further comprising a device arranged in the beam path downstream of the electromagnetic radiation source, wherein the device influences the electromagnetic radiation so that electromagnetic radiation of a specific wavelength penetrates the medium and reaches the detector.

3. The sensor according to claim 1, wherein the medium is an aqueous solution so that the concentration of at least one substance in the aqueous solution can be detected.

4. The sensor according to claim 1, wherein the electromagnetic radiation source is a multi-color luminescence diode providing the different wavelengths.

* * * * *